United States Patent [19]

Schulze et al.

[11] Patent Number: 5,728,109

[45] Date of Patent: Mar. 17, 1998

[54] SURGICAL KNOT AND METHOD FOR ITS FORMATION

[75] Inventors: Dale R. Schulze, Lebanon, Ohio; Troy A. McMillen, Champaign, Ill.

[73] Assignee: Ethicon Endo-Surgery, Inc., Cincinnati, Ohio

[21] Appl. No.: 827,718

[22] Filed: Apr. 8, 1997

[51] Int. Cl.$^6$ .................................................. A61B 17/04
[52] U.S. Cl. ........................... 606/139; 606/144; 606/148; 289/1.2; 289/1.5; 289/17
[58] Field of Search ....................... 606/144, 148, 606/139; 289/1.2, 1.5, 17

[56] References Cited

U.S. PATENT DOCUMENTS

| | | | |
|---|---|---|---|
| 2,012,776 | 8/1935 | Roeder | 128/326 |
| 2,566,625 | 9/1951 | Nagelmann | 128/326 |
| 3,090,386 | 5/1963 | Curtis | 126/334 |
| 3,177,021 | 4/1965 | Benham | 289/17 |
| 5,279,067 | 1/1994 | Tollison | 289/1.2 |
| 5,320,629 | 6/1994 | Noda et al. | 606/139 |
| 5,405,352 | 4/1995 | Weston | 289/1.2 |
| 5,573,286 | 11/1996 | Rogozinski | 289/12 |
| 5,643,293 | 7/1997 | Kogasaka et al. | 606/148 |

FOREIGN PATENT DOCUMENTS 912619  4/1994  Germany .

OTHER PUBLICATIONS

Howard T. Sharp, M.D., James H. Dorsey, M.D., John D. Chovan, Ph.D., P.E., Patrice M. Holtz, R.N., M.S. "The Effect of Knot Geometry on the Strength of Laparoscopic Slip Knots", *Obstetrics & Gynecology*, 1996, pp. 88:408–411.

John E. Meilahn, M.D., "The Need for Improving Laparoscopic Suturing and Knot–Tying", *Journal of Laparoendoscopic Surgery*, vol. 2, No. 5, 1992, pp. 267–268.

D.D. Gaur M.S. FRCS(Eng), "Manual laparoscopic suturing and knot tying made easy", ©1996 Blackwell Science Ltd, pp. 29–33.

Resad Pasic, M.D., Ph.D., Ronald L. Levine, M.D., "Laparoscopic Suturing and Ligation Techniques", Nov. 1995, vol. 3, No. 1 *The Journal of the American Association of Gynecologic Laparoscopists*, pp. 67–79.

Sung–Tao Ko and Mohan C. Airan, "Therapeutic laparosscopic suturing techniques", *Surgical Endoscopy*, (1992)6:41–46.

Thierry Vancaillie, M.D., Ernst H. Schmidt, M.D., "Therapeutic Laparoscopy", from *The Journal of Reproductive Medicine* pp. 891–894.

Zoltan Szabo, Ph.D., FICS, and George Berci, M.D., FACS, FRCS Ed (Hon), "Extracorporeal and Intracorporeal Knotting and Suturing Techniques" *Gastrointestinal Endoscopy Clinics of North America*, pp. 367–373.

Raoul Graumont, John Hensel "Enclyclopedia of Knots and Fancy Rope Work" Plates 30–49.

(List continued on next page.)

*Primary Examiner*—Michael Buiz
*Assistant Examiner*—Daphna Shai
*Attorney, Agent, or Firm*—Matthew S. Goodwin

[57] ABSTRACT

An improved method of forming a non-slip surgical knot for fastening tissue, and the knot prepared by the improved method, are disclosed. A partially tied knot which has a first loop and knot loops formed about the first loop to create a common loop core receiving the first loop is initially provided. The distal end of the suture filament from which the partially tied knot is made is passed through the tissue, and it is then fed through the first loop to form a tissue-fastening loop. The improvement involves pulling the first loop and a portion of the suture filament through the common loop core, thus eliminating the first loop and forming a distal loop positioned adjacent the common loop core. When this improved method is used to form the non-slip knot, a knot with a consistently high knot security can be formed without the need to provide a tension on the suture filament which exceeds the breaking strength of the suture.

12 Claims, 9 Drawing Sheets

OTHER PUBLICATIONS

Howard T. Sharp, M.D., James H. Dorsey, M.D., John D. Chovan, Ph.D., P.E., Patrice M. Holtz, R.N. "A Simple Modification to Add Strength to the Roeder Knot" pp. 305–307 Feb., 1996, vol. 3, No. 2 from *The Journal of the American Associates of Gynecologic Laparoscopists*.

Mike Kozminski, M.D., William H. Richards, III, M.D. "Fly–Casting Method of Introcorporeal Laparoscopic Knot Tying", pp. 577–578, from *Urology®*, Oct. 1994, vol. 44, No. 4.

J. L. Pennings, T. Kenyon, L. Swanstrom "The knit stich" from *Surgical Endoscopy* (1995) 9:537–540.

Harry Reich, M.D., H. Courtenay Clarke, M.D., Lisa Sekel, CST "Instruments & Methods", from *Obstet Gynecol* 1992;79:143–147.

Nathaniel J. Soper, M.D., FACS, and John G. Hunter, M.D., FACS "Suturing and Knot Tying in Laparoscopy" *Surgical Clinics of North America*, Oct. 1992 pp. 1139–1153.

S. Kitano, M.D., T. Yoshida, M.D., T. Bandoh, M.D., K. Shuto, M.D., K. Nakashima, M.D. & M. Kobayashi, M.D., "Knot tying intracorporeally at laparoscopic surgery facilitated with newly designed forceps" © 1996 *Blackwell Science Ltd*.

SURGICAL KNOT AND METHOD FOR ITS FORMATION

BACKGROUND OF THE INVENTION

This invention relates to a surgical knot made from a suture filament, and the method by which the knot is made. In particular, the invention relates to such a surgical knot which is particularly adapted for deployment during minimally invasive surgical procedures where access to the surgical site is limited.

A mainstay of surgical practice has been and will continue to be the formation and placement of surgical knots from suture filament to fasten tissue during an operative procedure. Numerous surgical knots have been developed over an appreciable period of time, and the an of forming and tying knots for surgical applications is a critical skill which a surgeon must possess to perform an operation safely and efficiently. Accordingly, the art is extensively developed. See, for example, Tissue Approximation in Endoscopic Surgery, Alfred Cuschieri, Zoltan Szabo, Times Mirror International Publishers, 1995, which describes numerous surgical knots made from suture filament to facilitate the approximation of tissue during surgery.

The art of surgical knots is also well represented in the patent literature. U.S. Pat. No. 2,012,776 discloses a surgical instrument for facilitating the placement of various forms of slip knots made from surgical filament. The inventor named on the '776 patent, H. A. Roeder, developed the "Roeder Knot" which is a surgical knot which is frequently used in practice today. More recently, U.S. Pat. No. 5,573,286 discloses a surgical knot of suture Strand particularly adapted for orthopedic applications. The preferred embodiment described in the '286 patent is directed to tying the knot to a bone.

Early on, it was recognized that the deployment and placement of surgical knots within a remotely accessible surgical site could be difficult, cumbersome and often unreliable. Accordingly, instrumentation was developed to facilitate the placement of knots in remote locations. Cleverly, a pre-tied knotted loop of suture was often used to reduce the number of steps required to form the tightened knot. For example, U.S. Pat. Nos. 2,566,625 and 3,090,386 describe surgical devices which are adapted to support a pre-tied knotted loop of suture for suturing or ligating tissue, particularly during procedures where the tissue desired to be manipulated is difficult to More recently, instrumentation has been developed for facilitating the placement of knots particularly during minimally invasive surgical procedures. In particular, U.S. Pat. No. 5,320,629 discloses the formation of a pre-tied knotted loop of suture, and the placement of the pre-tied knotted loop on a surgical device for facilitating the tightening of the loop to approximate tissue during endoscopic surgical procedures. German Patent No. 912619 also discloses a device similar to that disclosed in the '629 patent.

Although the art of surgical knots is well developed, and surgical devices for facilitating the placement of tightened knots from a pre-tied knotted loop of suture have also been developed for application at remote surgical sites, there are problems which still need to be addressed. In particular, in those surgical procedures where access to the site is limited, for example during minimally invasive procedures such as endoscopic surgical procedures, the knots which are deployed are routinely slip knots which have poor knot security. If knot security is poor, then the approximated tissue may not be held for a sufficient period of time to promote adequate wound healing. Additionally, during minimally invasive procedures, the pre-tied knotted loops of suture which have been described in the prior art devices can be difficult to efficiently tighten for final deployment.

Therefore, in minimally invasive surgical procedures where access to the surgical site is limited, what is needed is a surgical knot formed from a suture strand which will yield enhanced suture knot security. The knot should be relatively simple in construction and should be easy to form the tightened knot from a pre-tied knotted loop of suture. The formation of the knot from the pre-tied knotted loop of suture should provide a consistently strong knot security each time the knot is placed to enable even an inexperienced surgeon to confidently and efficiently place a secure suture knot. Additionally, the surgical knot should not only have enhanced suture knot security when formed, but also long term security to maintain tissue in its approximated state for a sufficient period of time to promote adequate wound healing. Finally, it would be ideal if the amount of tension which must be applied to the suture strand when the pre-tied knotted loop of suture is tightened is kept sufficiently low so that the suture does not break when the knot is deployed.

SUMMARY OF THE INVENTION

The invention is an improved method of forming a fully tied surgical knot for fastening bodily tissue. A partially tied knot is initially provided. The partially tied knot is formed from a suture filament having proximal and distal ends and proximal and distal lengths adjacent the proximal and distal ends. A first loop is formed between the proximal and distal lengths of the suture filament. A plurality of knot loops is formed about the first loop so as to form a common loop core receiving the first loop.

The distal end and the distal length of suture filament are passed through the bodily tissue to be fastened. Further, the distal end and the distal length of the suture filament are fed through the first loop so as to form a tissue-fastening loop. The partially tied knot is then converted into the fully tied knot.

The improvement in the method comprises the step of applying axial tension on the proximal length of the suture filament while the knot loops are supported during the conversion step. When axial tension is applied, the first loop and the distal length of the suture filament are pulled through the common loop core. In so doing, the first loop is eliminated, and a distal loop positioned adjacent the common loop core is formed.

The invention is also a non-slip surgical knot prepared by the improved method.

The improved method of this invention for forming a surgical knot provides a non-slip knot with enhanced suture knot security. The knot is formed from a partially tied knot which includes suture loops readily constructed. The fully tightened non-slip knot is easily formed from the partially tied knot.

When the improved method the invention is used to convert the partially tied knot to the fully formed non-slip knot, the first loop and distal length of suture filament are pulled through the common loop core of the partially tied knot. Each time this method is used, a knot is formed where the first loop is eliminated, and a distal loop is created. The elimination of the first loop and the creation of the second loop spontaneously cause a sound audible to the user to alert the user to the completion of the non-slip knot from the partially tied knot. Therefore, a novice can practice the improved method of this invention and deploy the completed knot consistently each time a knot is placed. The knot security will be strong consistently each time the knot is placed. In addition the tension on the suture filament to convert the partially tied knot into the fully formed knot is controlled because the knot loops can be loosely fastened about the first loop so that the common loop core is sufficiently sized. In this manner, the mount of axial tension necessary to pull the first loop through the common loop core can be controlled. Therefore, the mount of tension necessary to convert the knot can be controlled so that it does not exceed the breaking strength of the suture filament.

The improved method of this invention, and the surgical knot prepared by this method, can be practiced in any surgical application where it is necessary or desirable to fasten bodily tissue. Although the application of this invention is ideally suited for minimally invasive surgical procedures where access to the surgical site is limited, it can be readily applied to open surgical procedures as well.

BRIEF DESCRIPTION OF THE PREFERRED EMBODIMENTS

FIGS. 1–6 illustrate how a partially tied surgical knot can be made from a length of suture filament. The partially tied knot thus formed can be used in the practice of the various embodiments of this invention.

Figure 1:
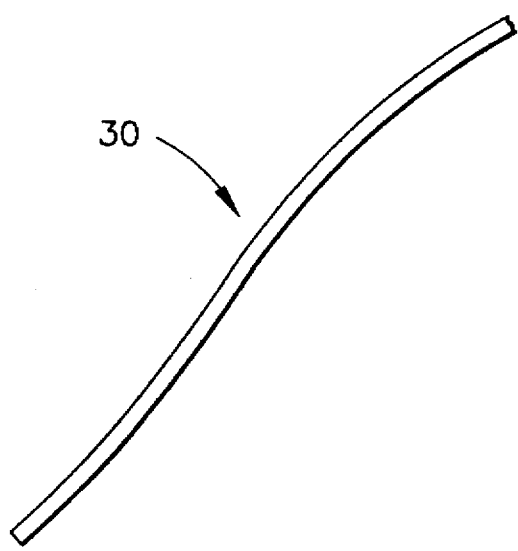
FIGS. 1–6 are perspective views illustrating the sequence of steps for forming a partially tied knot from a length of suture filament.

The suture filament 30 shown in FIG. 1 can be composed of any suture material currently used or hereafter developed. The suture filament may be a monofilament suture or a multifilament, braided suture. The suture filament, regardless of construction, may be non-absorbable or bio-absorbable, depending on the particular application for which the suture is being used to fasten tissue.

The length of suture filament 30 has proximal and distal ends, 31 and 32, respectively. Adjacent the proximal end, there is a proximal length 33 of suture filament. Correspondingly, adjacent the distal end of the suture filament, there is a distal length 34 of the suture filament.

Figure 2:
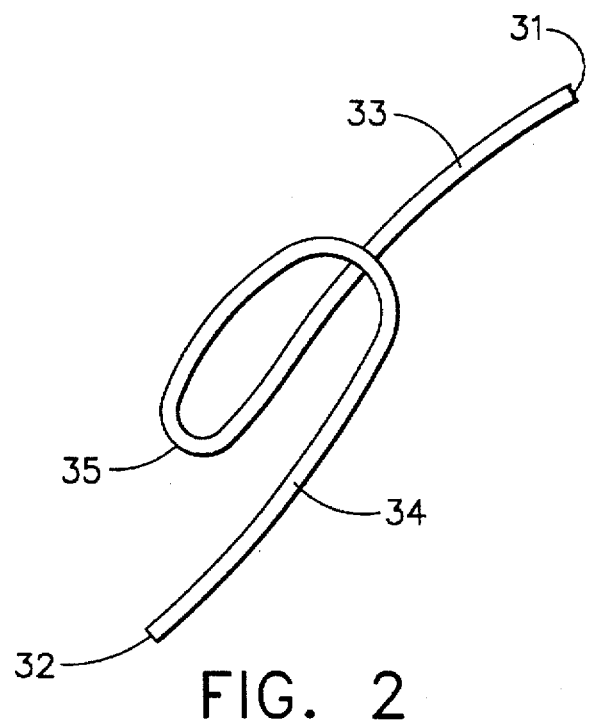
Figure 3:
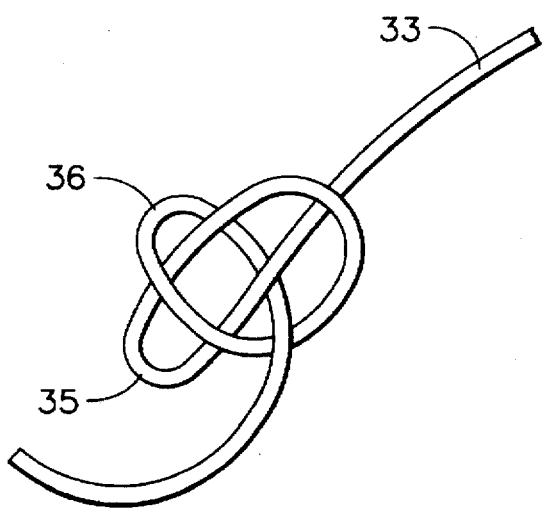
Figure 4:
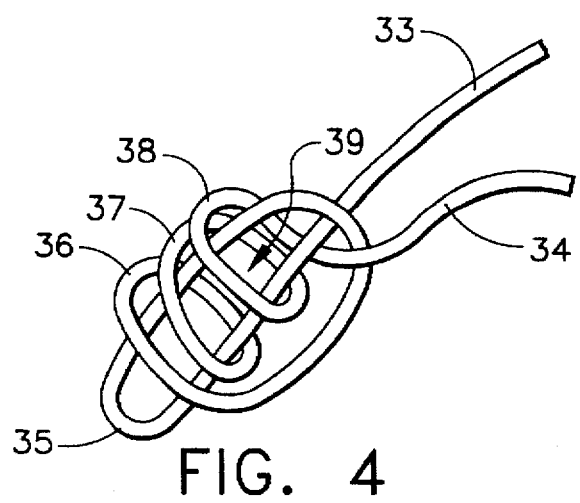

As shown in FIG. 2, a first loop 35 is formed by manipulating the distal length 34 of the suture filament. Now looking at FIG. 3, while the proximal length 33 of the suture filament remains fixed, the distal length is manipulated to form a second loop 36 wrapped generally transversely around the first loop 35. Third and fourth loops, 37 and 38, respectively, are likewise formed about the first loop as depicted in FIG. 4. The second, third and fourth loops are generally parallel to each other and are oriented generally transversely to the first loop. For purposes of describing this invention, these loops may be referred to collectively as the "knot loops". The number of knot loops may vary depending on the particular application for which the knot is used. In the illustrated embodiment, the second, third and fourth loops together form a common loop core 39 which receives the first loop 35.

Figure 5:
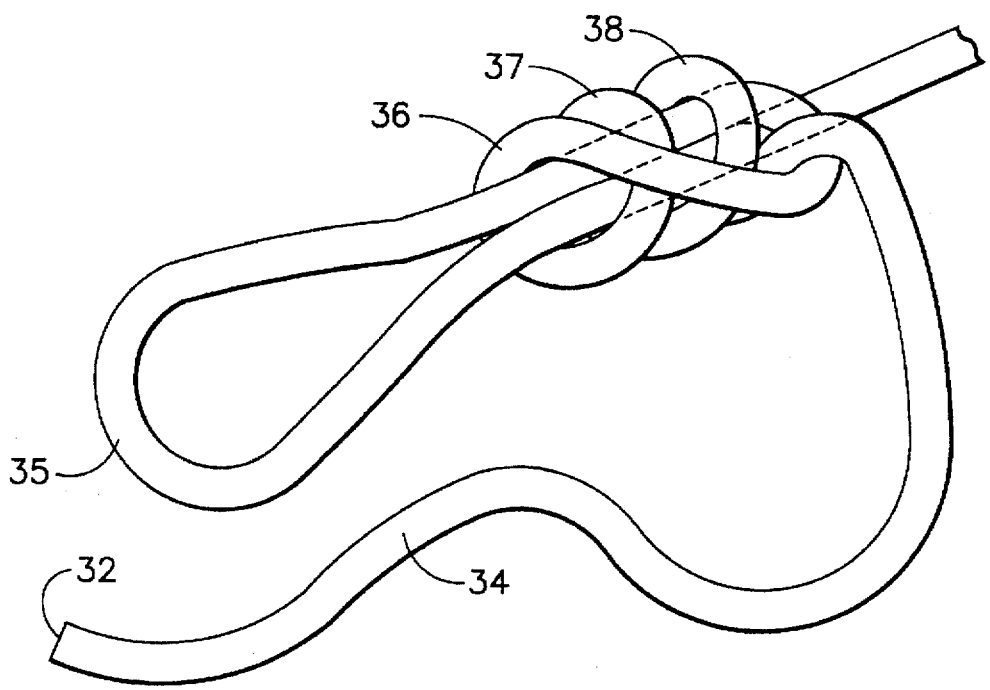

Reviewing FIG. 5, the loosely formed knot is tightened by applying tension on the distal length 34 of the suture filament. In so doing, the second, third and fourth loops tighten down on the first loop, and thus the first loops is securely received in the common loop core.

Figure 6:
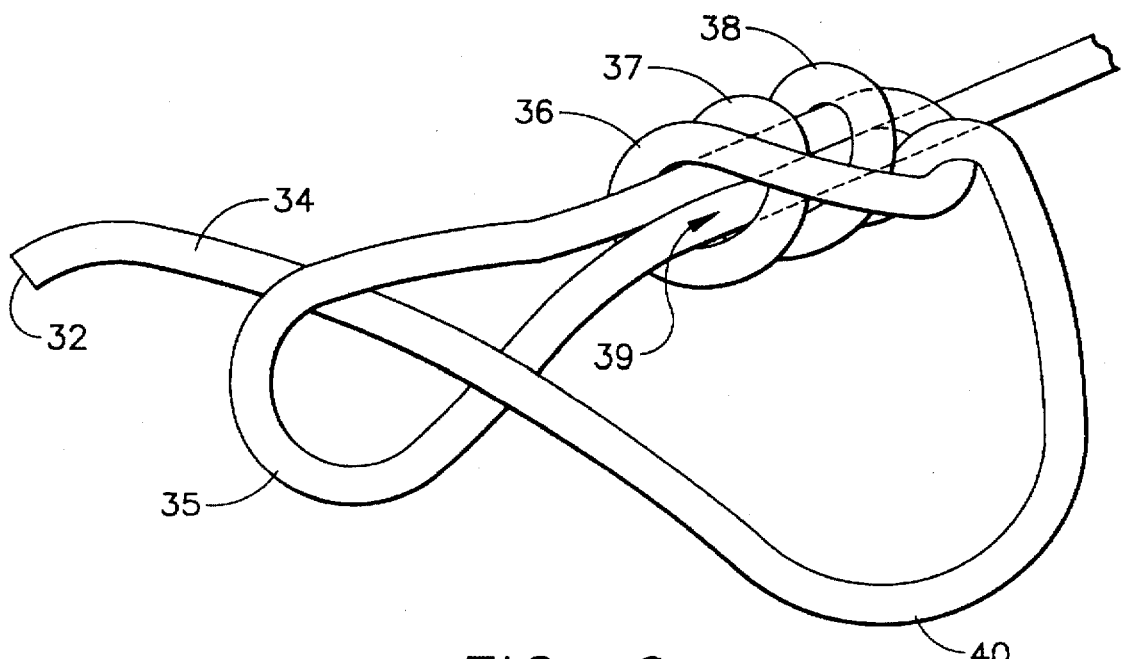

As depicted in FIG. 6, a tissue-fastening loop 40 can be formed by passing the distal end 32 and the distal length 34 of the suture filament through the first loop 35.

Figure 7:
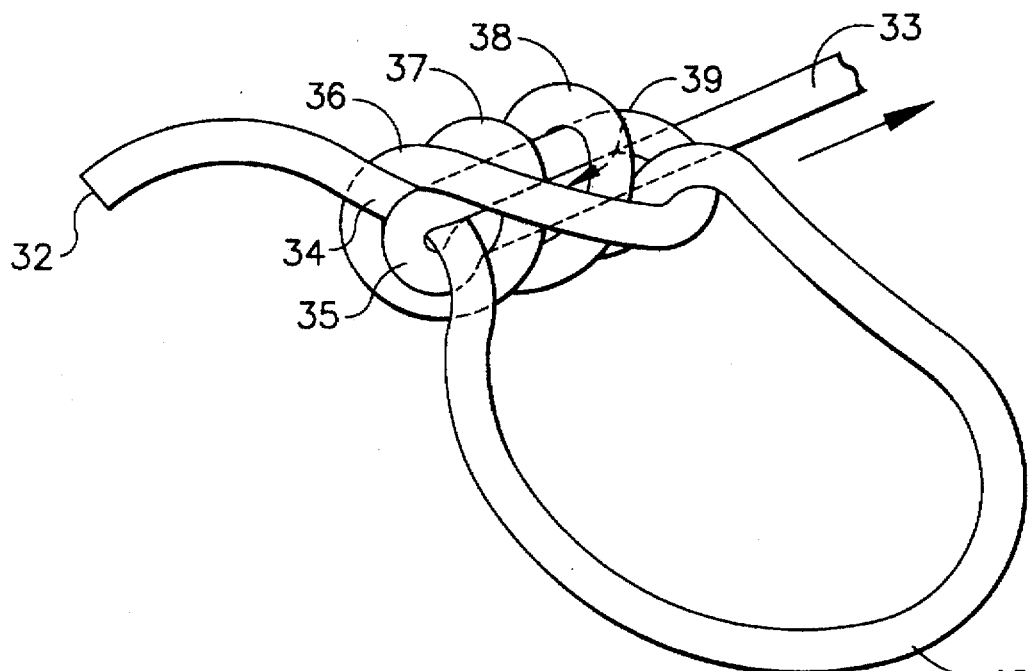
FIGS. 7–8 are perspective views of a preferred embodiment of the invention illustrating the steps to convert the partially tied knot depicted in FIG. 6 into a non-slip surgical knot.

To form the knot represented by a first embodiment of this invention, the partially tied knot of FIG. 6 is taken, and tension on the proximal length 33 of the suture filament is applied in the proximal direction as indicated by the arrow in FIG. 7. To facilitate forming the knot, the surgeon ideally holds his fingertips against the proximal side of the knot loops while tension is applied to the proximal length 33 of the suture filament. Alternatively, as described in the embodiments below, an instrument can be used to hold the knot loops in place. As tension is applied, the first loop 35 begins to be pulled through the common loop core 39 of the knot. When the first loop has sufficiently diminished in size from that shown in FIG. 6, it snares the distal length 34 of the suture filament. With continuing proximal tension on the proximal length of the suture filament, the first loop and the distal length of filament are pulled through the common loop core 39. When the first loop and distal length of filament emerge from the fourth loop 38, an audible "clicking" sound will alert the user that the completed knot has been formed.

Although the partially tied knot illustrated in FIG. 6, often referred to as a "blood" knot, is the preferred partially tied knot for conversion into the fully formed, non-slip knot of this invention, other slip knots described in the literature can be used. The key characteristic for the acceptability of other partially tied knots is a common loop core (exemplified in FIG. 6 as common loop core 39) allowing passage of suture filament through the core. See, for example, The Encyclopedia of Knots and Fancy Ropework, R. Graumont and J. Hensel, Fourth Edition, Cornell Maritime Press. Suitable partially tied knots are shown in this book as numbers 102, 185, 227 and 349 on pages 71, 83, 87 and 102, respectively.

Figure 8:
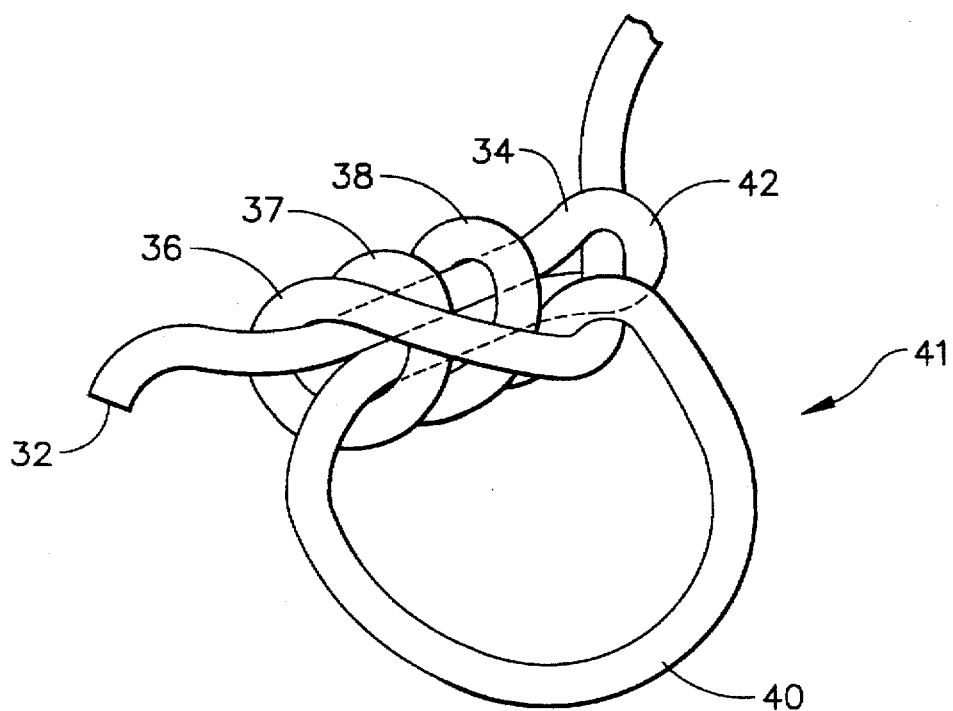

As depicted in FIG. 8, the completed surgical knot of this invention is a non-slip knot 41. The first loop has been eliminated, and a distal loop 42 positioned adjacent to the fourth loop 38 is formed from a portion of the distal length of the suture filament. The tissue loop 40, which is used to fasten tissue, consequently becomes rigidly fixed and secure. Tension applied to the loop 40 due to the tendency of the fastened tissue to expand or pull apart may result beneficially in further tightening of the non-slip knot.

Figure 9:
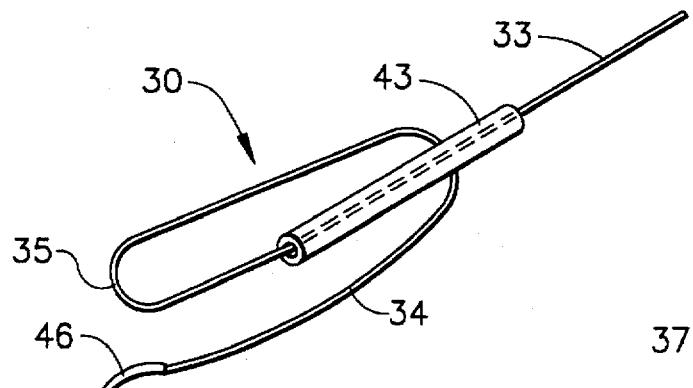
FIGS. 9–10 are perspective views illustrating the formation of the partially tied knot of FIG. 6, which includes a surgical needle attached to the suture filament, about a core tube.
Figure 10:
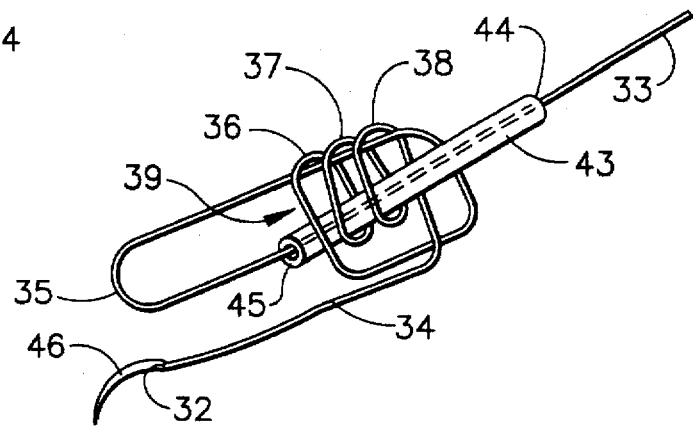

Referring to FIGS. 9 and 10, there is shown the formation of the partially tied knot depicted in FIGS. 1-6, formed about a core tube 43. The core tube facilitates the placement of the partially tied knot adjacent tissue desired to be fastened, as well as the conversion of the partially tied knot into the completed non-slip knot shown in FIG. 8. The core tube has proximal and distal ends, 44 and 45, respectively. A surgical needle 46 is attached to the distal end 32 of the surgical filament. The proximal length 33 of the filament is passed through the core tube. The length of suture filament exceeds the length of the core tube so that the proximal length of the suture filament may extend from the proximal end 44 of the core tube. Additionally, a sufficient mount of suture filament represented by its distal length 34 exits the distal end of the core tube so that it is possible to form the partially tied knot about the distal end 45 of the core tube. The first loop 35 and the subsequent knot loops represented by the second, third and fourth loops, 36, 37 and 38, are formed about the distal end of the core tube. Once formed, tension is applied to the distal length of the filament to tighten the knot loops about the distal end of the core tube.

Figure 11:
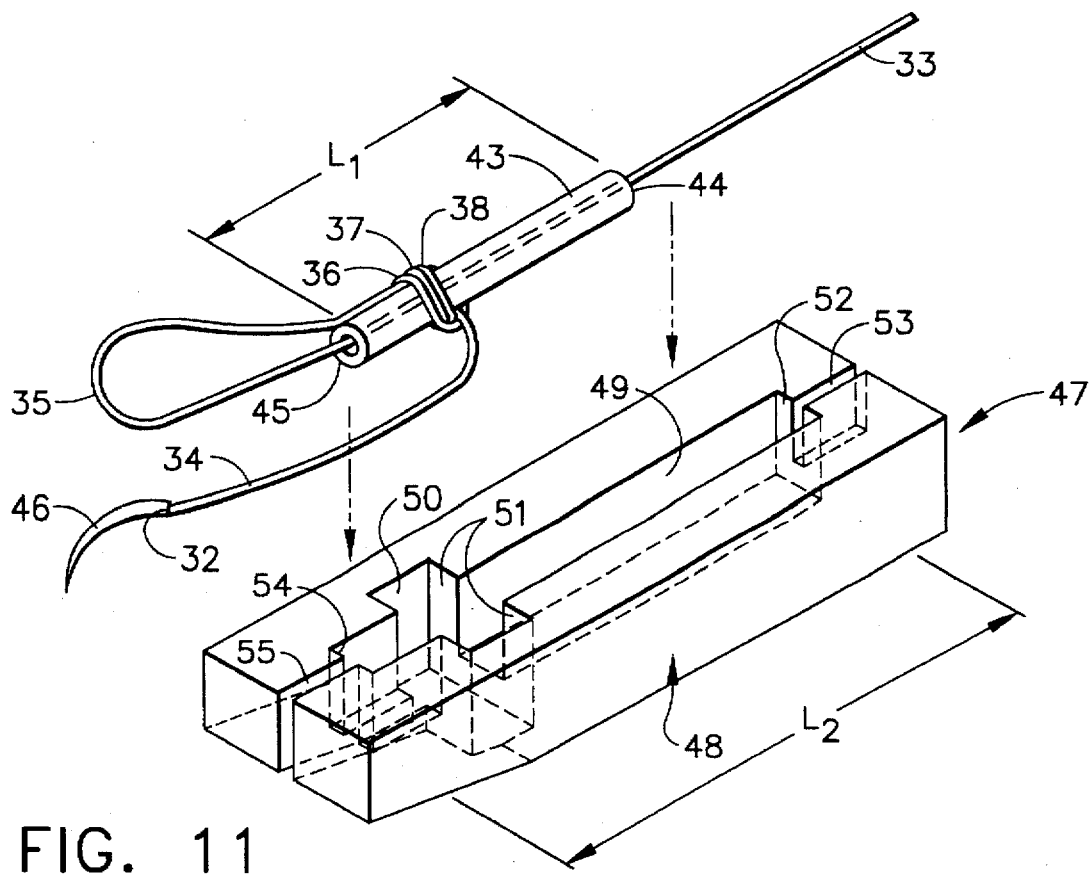
FIG. 11 is an exploded perspective view of another preferred embodiment of the invention illustrating the partially tied knot of FIG. 6 formed about the core tube depicted in FIGS. 9–10, in combination with a suture cartridge.

In another embodiment of the invention, the partially tightened knot formed about the core tube can be loaded into a suture cartridge 47 as illustrated in FIG. 11. The suture cartridge has an elongated body 48. A tube slot 49 for receiving the core tube 43 is embedded in the body of the cartridge. The body also contains a knot recess 50 which has a pair of stripping shoulders 51. Extending from a proximal edge 52 of the tube slot in a proximal direction is a filament slot 53. Correspondingly, extending from a distal edge 54 of the tube slot toward a distal end of the cartridge body is a loop slot 55. The length of the core tube, designated as $L_1$ in FIG. 11, is less than the length of the tube slot, designated as $L_2$ in FIG. 11.

Figure 13:
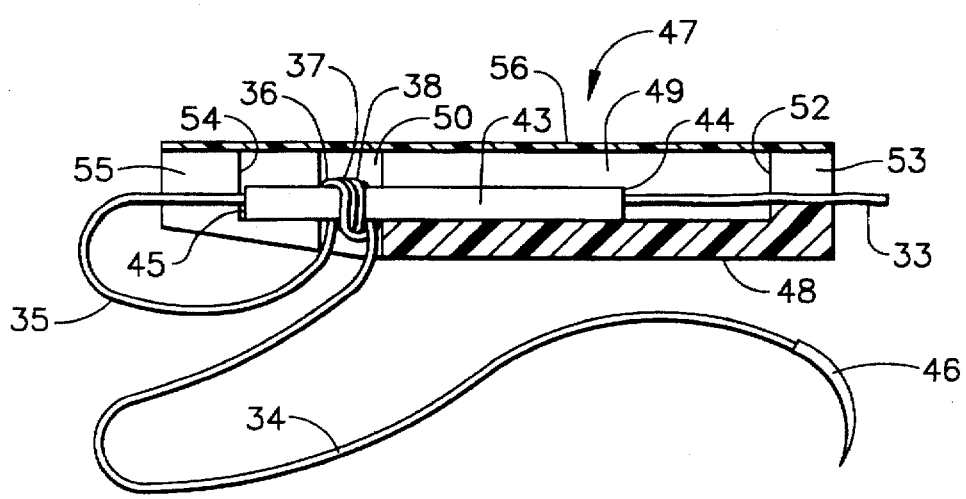
FIG. 13 is a section view of the assembly depicted in FIG. 12 taken along line 13—13 of that Figure.

When the partially tied knot is formed about the core tube 43, the knot loops are wrapped about the distal end 45 of the core tube. The free proximal end of the suture filament extends from the proximal end 44 of the core tube. The first loop 35 of the partially tied knot extends from the distal end of the core tube. When the core tube is loaded into the tube slot 49 of the cartridge body, the knot loops sit inside the knot recess and abut the stripping shoulders of the knot recess. A portion of the proximal length 33 of the suture filament rests in the filament slot 53 embedded in the body of the cartridge, and the remaining portion of the proximal length of the suture filament extends from the proximal end of the cartridge body. Correspondingly, the first loop 35 of the partially tied knot and the distal end 34 of the surgical filament are received in the loop slot 55. A substantial portion of the first loop and the distal length of suture filament extend outside of the cartridge body. In its original position as best illustrated in FIG. 13, the distal end 45 of the core tube is adjacent the distal edge 54 of the tube slot. Since the tube slot 49 has a length greater than that of the core tube 43, the core tube is capable of sliding proximally toward the proximal edge 52 of the tube slot. In this position, the knot is trapped in recess 50. The surgeon can then easily manipulate needle 46 and suture filament 34 without danger of prematurely deploying the knot.

Figure 12:
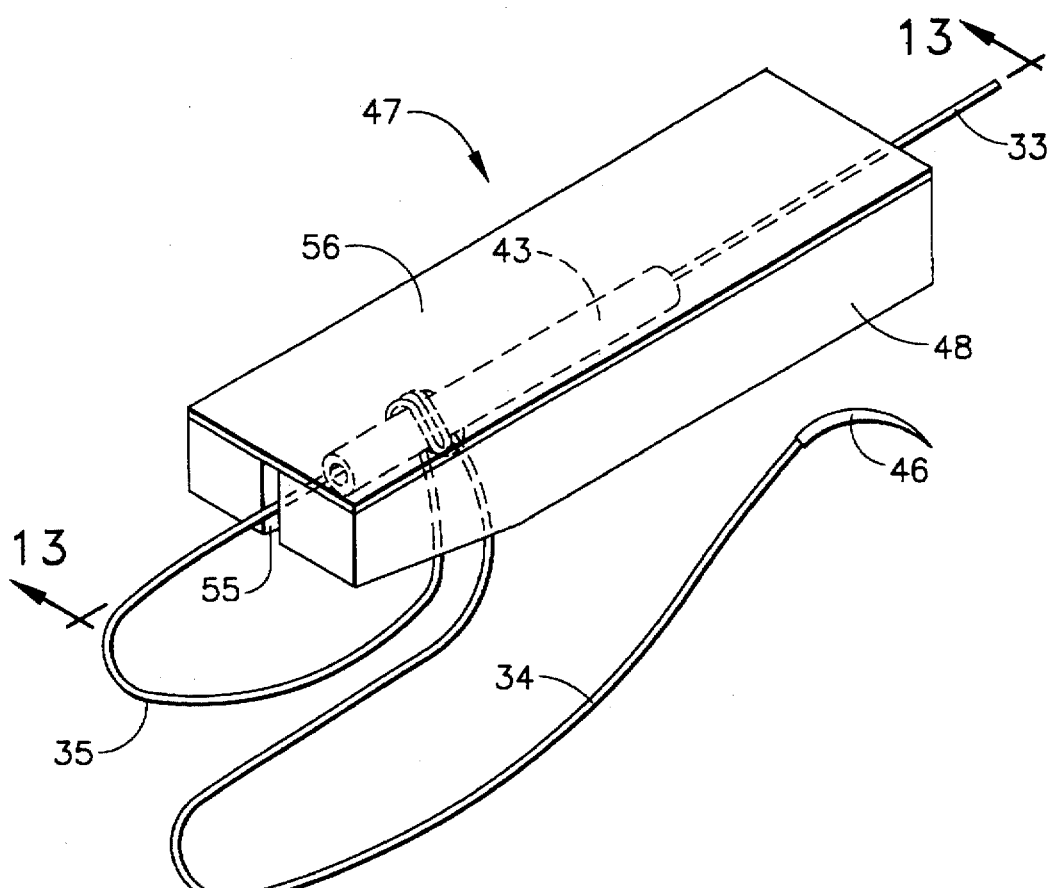
FIG. 12 is a perspective view in assembly of the combination depicted in FIG. 11, where the suture cartridge has a cartridge top.

When the core tube is loaded into the tube slot within the body of the cartridge, a cartridge top 56 can be mounted onto the cartridge body 48 as shown in FIG. 12. When the cartridge top is mounted, the core tube 43 is fully enclosed within the cartridge.

Figure 14:
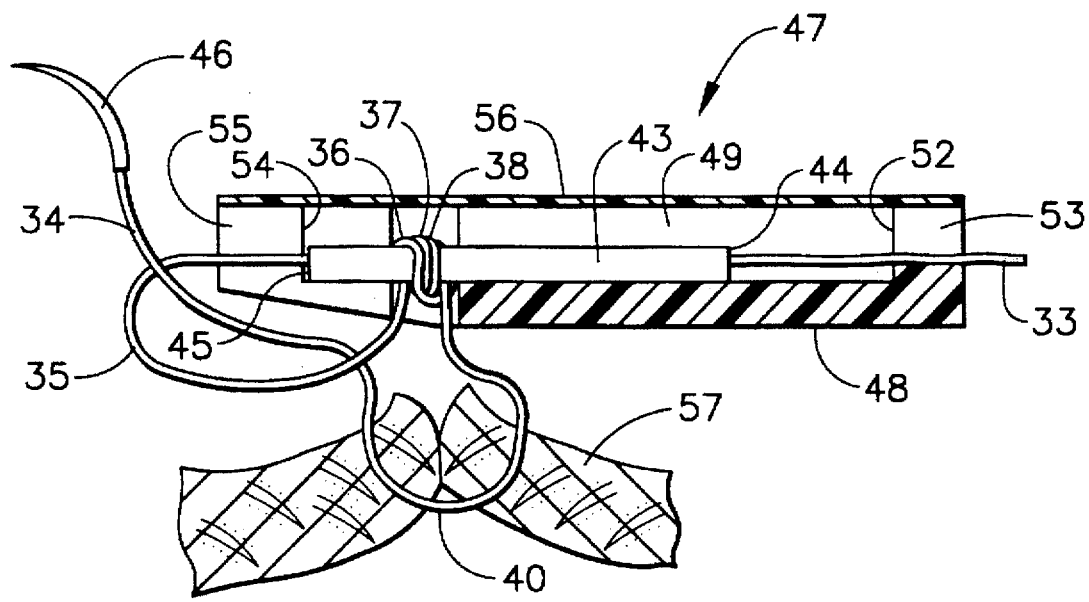
FIGS. 14–15 are section views of the assembly depicted in FIG. 13, including a fragmentary section of tissue, illustrating the use of the partially tied knot to fasten tissue and the steps necessary to form the completed non-slip surgical knot to securely fasten the tissue.
Figure 15:
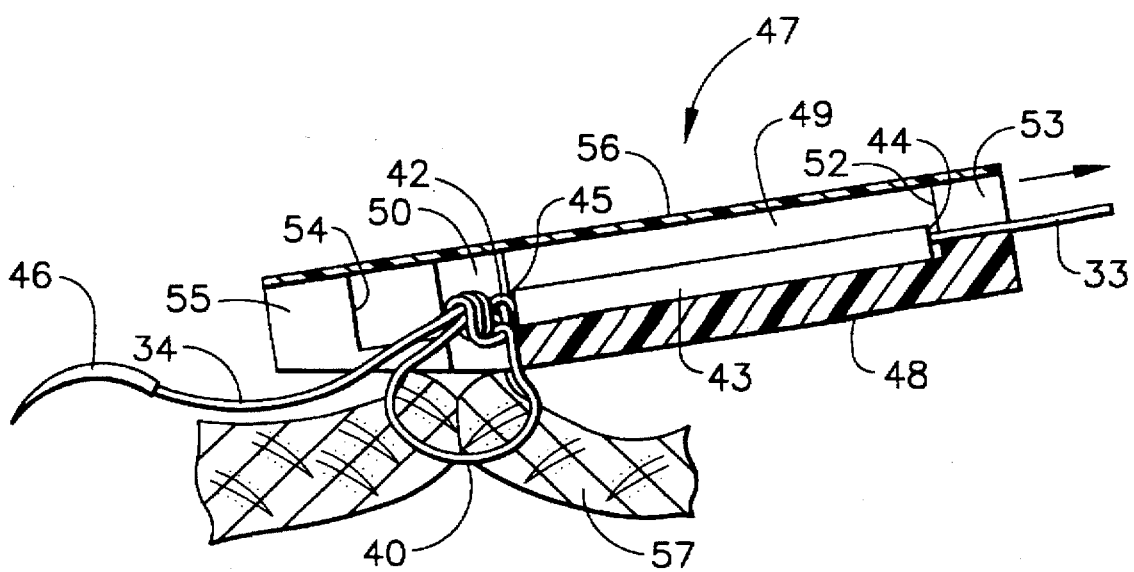

With the core tube fully enclosed within the suture cartridge, the partially tied knot wrapped about the core tube can be deployed to fasten desired bodily tissue as illustrated in FIGS. 14–15. The first step is to position the suture cartridge 47 adjacent bodily tissue 57 desired to be fastened. Next, the surgical needle 46 is passed through the tissue, and into and through the first loop 35 to form the tissue loop 40. The size of the tissue loop is adjusted to provide the appropriate tension on the opposed tissue sections of the bodily tissue 57 desired to be fastened; once the knot is completed to from the non-slip knot, the tissue loop becomes rigidly fixed and further adjustment is unavailable. When the tissue loop 40 is formed and appropriately sized, proximal tension is applied to the proximal length 33 of the suture filament in the direction of the arrow as depicted in FIG. 15. The completed knot is formed when sufficient tension is felt or applied to the proximal length 33.

Advantageously, when tension is applied to the proximal length 33 of the filament, the first loop is pulled and eventually applies a proximal force against the distal end 45 of the core tube 43, causing it to slide proximally as shown in FIG. 15. Since the knot loops abut against the stripping shoulders in the knot recess 50, the knot loops remain stationary even though the core tube slides proximally. When the core tube slides to a position where it is adjacent the proximal edge 52 of the tube slot 49, the knot loops are stripped from the distal end 45 of the core tube. The knot is then fully formed, and the user can remove the cartridge top 56, cut the remaining proximal and distal lengths of suture filament, and remove the core tube. Alternatively, the proximal and distal lengths of suture filament can be exposed without removing cartridge top 56 by releasing the tension on proximal length 33 and pulling the cartridge proximally, thus allowing a portion of the proximal and distal lengths of suture filament contained in the core tube 43 to extend distally from recess 50.

The suture cartridge 47 is advantageous because it is readily adaptable to conventional open and endoscopic instruments, and thus readily facilitates the formation of the knot. The suture cartridge may be disposable, or it can be used on multiple patients. When used on multiple patients, a plurality of disposable core tubes, including the partially tied knot wrapped about the tube, can be loaded serially into the suture cartridge to provide for the placement of numerous surgical knots to fasten tissue using a single suture cartridge.

Figure 21:
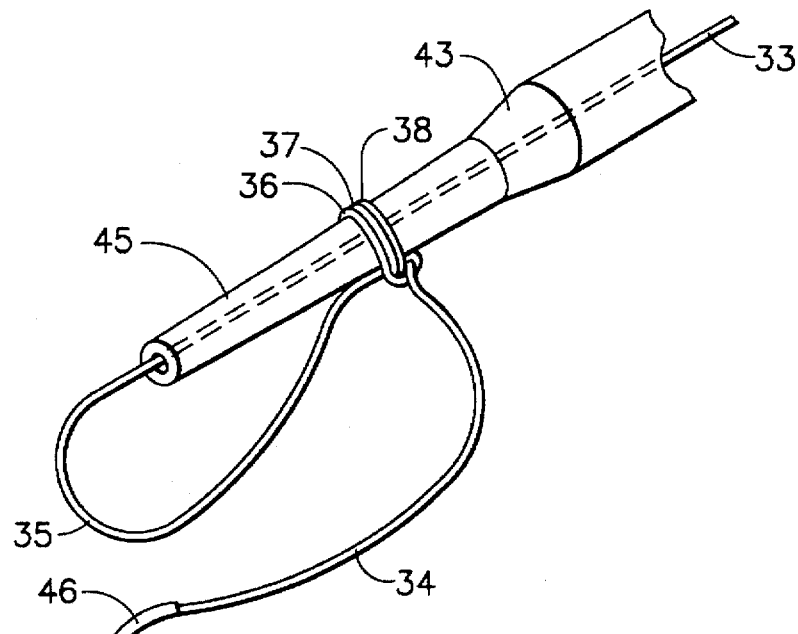
FIGS. 21–23 illustrate the use of the partially tied knot depicted in FIG. 6 formed about a tapered core tube to fasten tissue when the partially tied knot is converted to a completed, non-slip surgical knot.
Figure 22:
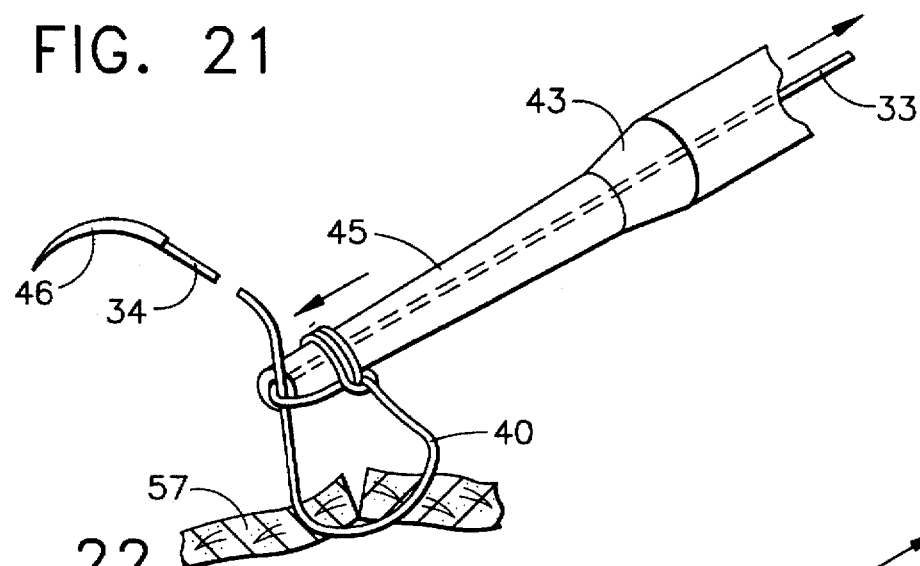
Figure 23:
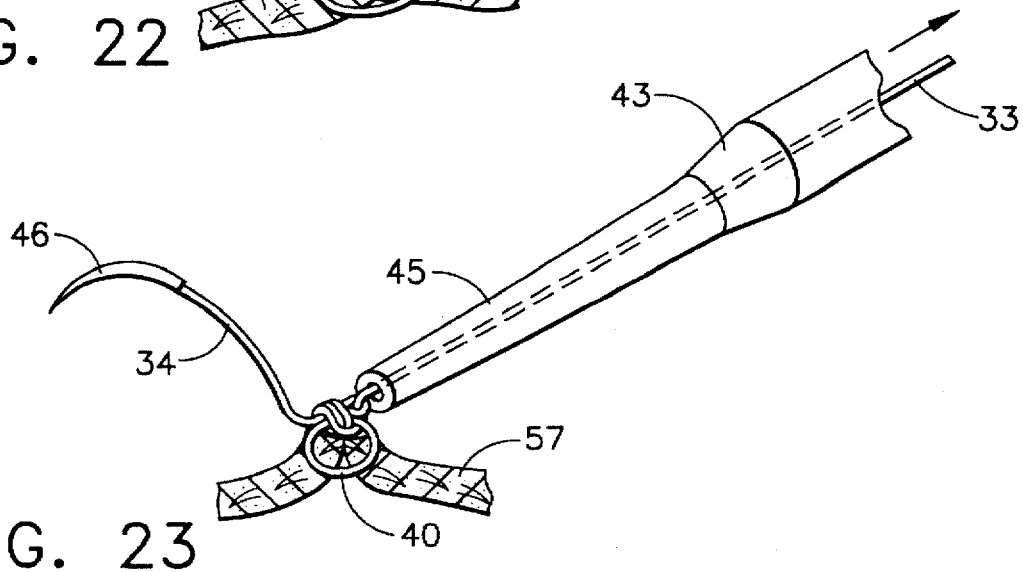

In another embodiment of the invention, the partially tied knot is wrapped about the core tube to facilitate the conversion of the knot to the completed, non-slip knot to fasten tissue. This similar embodiment is illustrated in FIGS. 21–23. The one key difference between what is shown here and that illustrated in FIGS. 9–15 is that the core tube has a tapered distal end. For convenience, the same numbers have been used to identify component pain in FIGS. 21–23 as those used in FIGS. 9–15.

Figure 16:
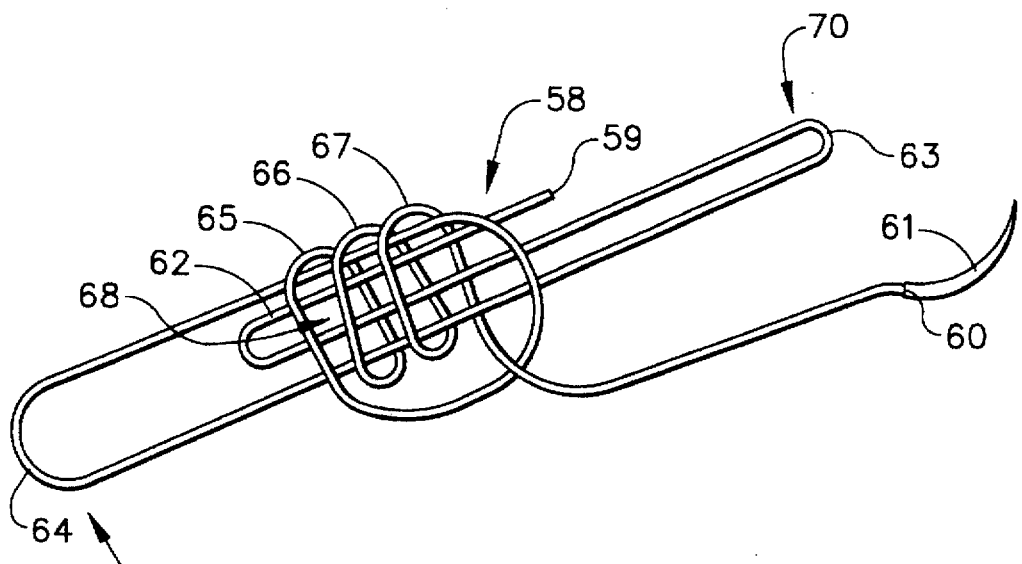
FIGS. 16 and 17 are perspective views of yet another preferred embodiment of the invention depicting the formation of a different partially tied surgical knot from a length of suture filament.
Figure 17:
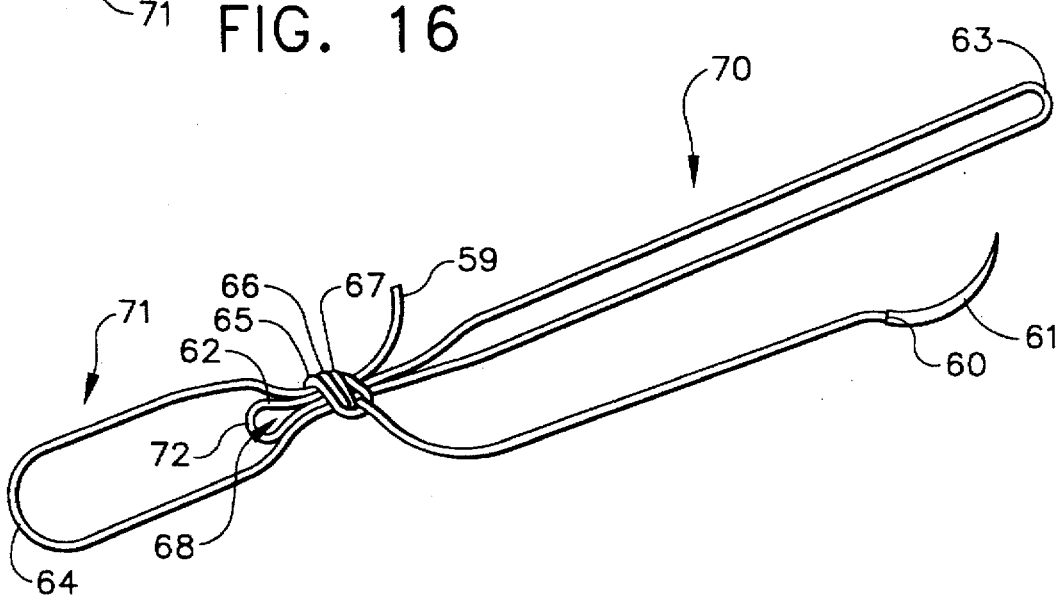

In yet another embodiment of this invention, a partially tied surgical knot is illustrated in FIGS. 16–17. The knot is made from a suture filament 58 which has a proximal end 59 and a distal end 60. A surgical needle 61 is attached to the distal end. The distal end of the filament is manipulated to form the knot while the proximal end of the filament is held stationary. A core loop 62, proximal loop 63 and first loop 64 are initially formed. The proximal loop is at a first end 70 of the knot, and the first loop is at an opposite end 71 of the knot. The core loop is situated between the first and opposite ends of the knot. Knot loops, in the preferred embodiment consisting of second, third and fourth loops, 65, 66, and 67, are formed about the proximal loop 63 and the first loop 64. The knot loops together form a common loop core 68. The core loop is positioned within the common loop core. When tension is applied to the distal end of the surgical filament while the proximal end of the knot loops is supported, the knot loops are tightened. The knot loops are tightened about the first loop, proximal loop and core loop. When tightened, as shown in FIG. 17, the first loop, core loop and proximal loop are securely received in the knot loops, and the partially tied knot is formed.

Referring specifically to FIG. 17, the core loop 62 has a free proximal end 69 extending from the common loop core 68 toward the first end 70 of the knot. The core loop has a loop end 72 which extends from the common loop core in an opposite direction toward the opposite end 71 of the knot. The loop end 72 of the core loop 62 is disposed inside the first loop 64.

The partially tied knot of FIG. 17 can be converted to a completed non-slip knot when axial tension is applied to the proximal loop in the proximal direction while the proximal end of the knot loops is supported. In a manner similar to the deployment of the knot best illustrated in FIGS. 1–8, the knot is converted when the first loop is pulled through the common loop core to form a distal loop. Advantageously, when tension is applied on the proximal loop, not only is the first loop pulled through the common loop core, but also the core loop is pulled through as well. This provides an advantage because the core loop creates a sufficient space represented by the common loop core to enhance the ease of passage of the first loop through the common core to form the completed knot. Easier passage reduces the amount of tension which is needed to be applied to the proximal loop to form the completed knot, and therefore increases the degree of control of the user when the knot is being deployed.

Figure 18:
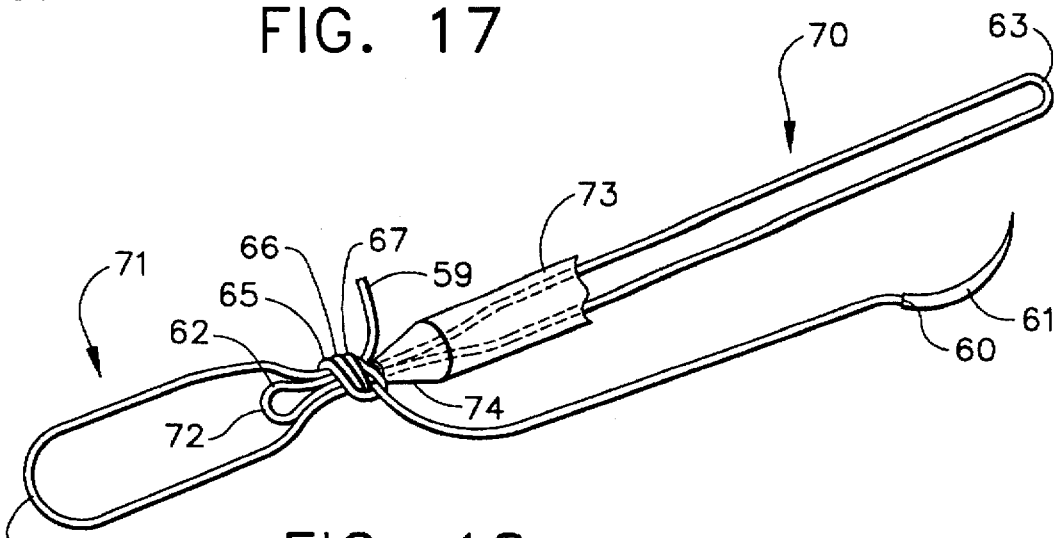
FIG. 18 is a perspective view of the partially tied knot depicted in FIG. 17 formed about a stripping tube.
Figure 19:
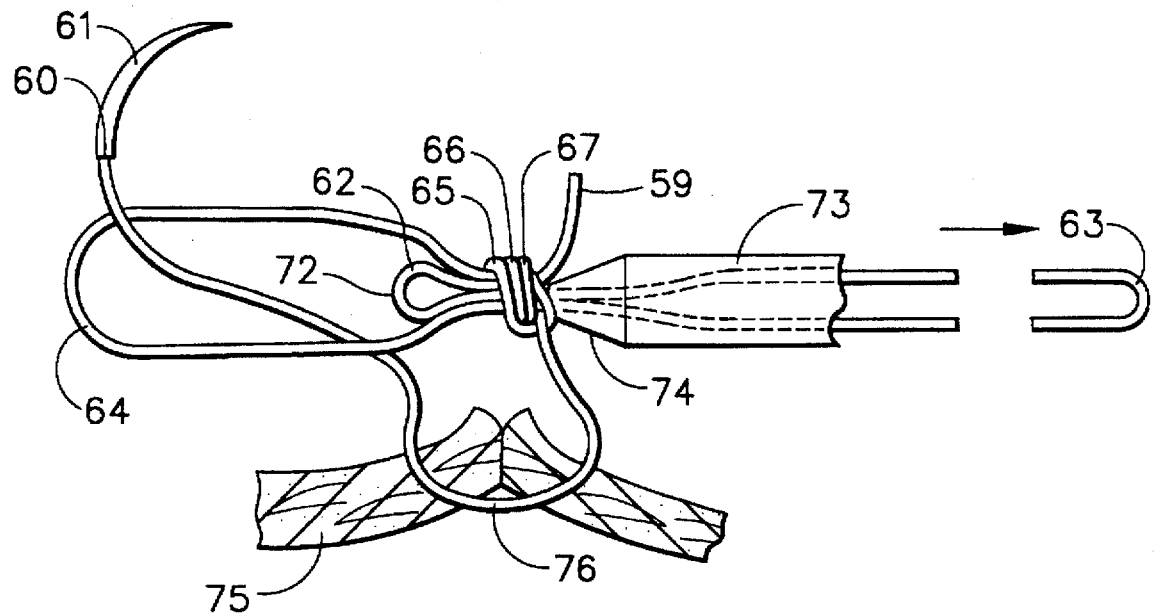
FIGS. 19–20 are side elevation views illustrating the use of the assembly depicted in FIG. 18 to form a completed, non-slip surgical knot to fasten tissue.
Figure 20:
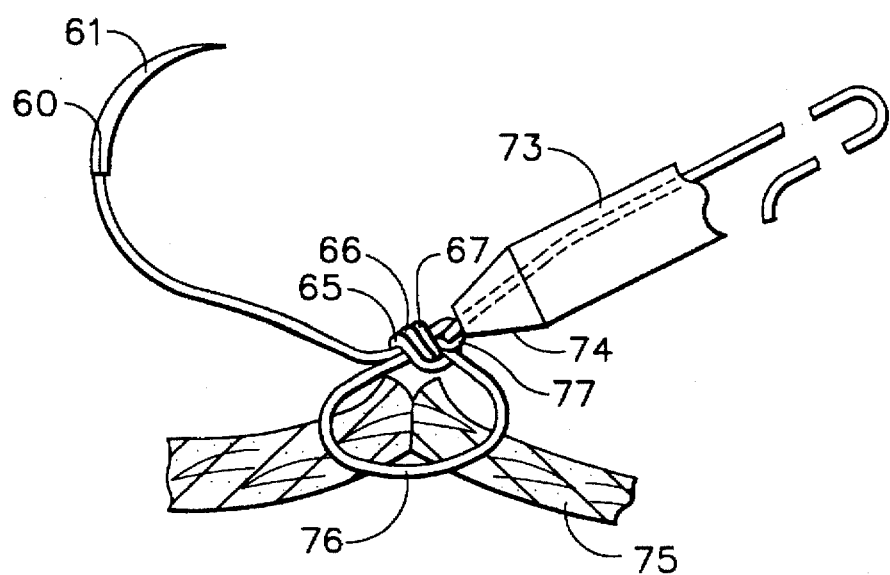

FIGS. 18–20 illustrate the use of the knot depicted in FIG. 17 to fasten tissue, where the knot is deployed in combination with a stripping tube 73. When the partially tied knot of FIG. 17 is formed, the proximal loop 63 is passed through the stripping tube. A portion of the proximal loop extends from a proximal end of the stripping tube. The proximal loop is passed through the stripping tube until the knot loops abut against the distal end of the snipping tube. Significantly, the snipping tube has a tapered distal end 74. The core loop and the first loop extend away from the tapered distal end of the tube. The opening at the distal end of the tube is smaller in diameter than the diameter of the knot loops. Consequently, when tension is applied on the proximal loop in the proximal direction, the knot loops will not pass into the snipping tube.

The conversion of the partially tied knot to the completed knot is performed in a manner substantially similar to that described in the previous embodiments.

Referring now to FIGS. 19–20, the stripping tube 73 is positioned adjacent bodily tissue 75 desired to be fastened. The surgical needle 61 is drawn through the tissue. A tissue loop 76 is formed when the surgical needle and distal end of the filament are fed through the first loop 64. Again, it is important to adjust the size of the tissue loop to provide for appropriate tensioning of the fastened tissue before the knot is fully deployed. When the desired tissue loop is formed, tension on the proximal loop 63 is applied in the proximal direction as indicated by the arrow in FIG. 19 to pull the core loop 62 and the first loop 64 through the common loop core. When the first loop emerges from the fourth knot loop 67, the distal loop 77 is formed, and the completed, non-slip knot has been created.

The different embodiments of this invention are representative of the preferred embodiments of the invention. These embodiments are merely illustrative. The scope of the invention should not be construed to be limited by these embodiments, or any other particular embodiments which may come to mind to those skilled in this art. Instead, the reader must refer to the claims which appear below to determine the scope of the invention.

What is claimed is:

1. An improved method of forming a fully tied surgical knot for fastening bodily tissue wherein:

a) a partially tied knot is provided, said partially tied knot being formed from a suture filament having proximal and distal ends and proximal and distal lengths adjacent said proximal and distal ends, a first loop is formed between the proximal and distal lengths, and a plurality of knot loops is formed about said first loop so as to form a common loop core receiving said first loop;

b) the distal end and the distal length of said suture filament are passed through the bodily tissue to be fastened;

e) the distal end and the distal length of said suture filament are fed through said first loop so as to form a tissue-fastening loop; and d) said partially tied knot is converted into said fully tied surgical knot;

wherein the step of converting comprises the step of:
      applying axial tension on the proximal length of said suture filament while said knot loops are supported so as to pull said first loop and the distal length of said suture filament through said common loop core, thereby eliminating said first loop and forming a distal loop positioned adjacent said common loop core.

2. The improved method of claim 1 wherein said knot loops contain second, third and fourth loops.

3. A non-slip surgical knot prepared by the improved method of claim 2.

4. The improved method of claim 1 wherein a surgical needle is attached to the distal end of said suture filament.

5. The improved method of claim 1 wherein said partially tied knot is formed about a core tube.

6. The improved method of claim 5 wherein said knot loops are formed about said core tube, said first loop extends from a distal end of said core tube, and the proximal length of said suture filament is fed through said core tube so as to extend from a proximal end thereof.

7. The improved method of claim 6 wherein when axial tension is applied on the proximal length of said suture filament, said first loop is pulled through said core tube, and said knot loops slide off the distal end of said core tube.

8. The improved method of claim 7 wherein said knot loops are formed about the distal end of said core tube, and the distal end of said core tube is tapered.

9. A non-slip surgical knot prepared by the improved method of claim 7.

10. A non-slip surgical knot prepared by the improved method of claim 6.

11. A non-slip surgical knot prepared by the improved method of claim 5.

12. A non-slip surgical knot prepared by the improved method of claim 1.

* * * * *